(12) United States Patent
Zhou et al.

(10) Patent No.: US 9,320,816 B2
(45) Date of Patent: Apr. 26, 2016

(54) METHODS OF TREATING CELL CULTURE MEDIA FOR USE IN A BIOREACTOR

(75) Inventors: Joe Zhou, Shanghai (CN); Felix M. Solamo, Winnetra, CA (US)

(73) Assignee: Amgen Inc., Thousand Oaks, CA (US)

( * ) Notice: Subject to any disclaimer, the term of this patent is extended or adjusted under 35 U.S.C. 154(b) by 885 days.

(21) Appl. No.: 12/663,837

(22) PCT Filed: Jun. 12, 2008

(86) PCT No.: PCT/US2008/066745
§ 371 (c)(1),
(2), (4) Date: Apr. 23, 2010

(87) PCT Pub. No.: WO2008/157247
PCT Pub. Date: Dec. 24, 2008

(65) Prior Publication Data
US 2010/0203610 A1    Aug. 12, 2010

Related U.S. Application Data

(60) Provisional application No. 60/944,468, filed on Jun. 15, 2007.

(51) Int. Cl.
*C12N 13/00* (2006.01)
*A61L 2/00* (2006.01)
(52) U.S. Cl.
CPC ............. *A61L 2/0011* (2013.01); *A61L 2/0017* (2013.01)
(58) Field of Classification Search
CPC ..... A61L 2/0017; A61L 2/0011; C12N 13/00

USPC ........... 210/610, 615–618, 203, 200, 748.01, 210/748.1; 422/22, 24, 186, 186.3; 435/383, 41, 292.1
See application file for complete search history.

(56) References Cited

U.S. PATENT DOCUMENTS

| 6,090,588 | A  | * | 7/2000 | Kokjohn et al. ............. 435/71.2 |
| 6,989,264 | B2 | * | 1/2006 | Atkinson et al. ............. 435/239 |
| 7,420,183 | B2 |   | 9/2008 | Kaiser |
| 7,476,885 | B2 | * | 1/2009 | Garcia et al. ............. 250/504 H |
| 7,875,446 | B2 | * | 1/2011 | Kang et al. ................... 435/239 |
| 2003/0201230 | A1 | * | 10/2003 | Kopf ............................ 210/656 |
| 2004/0005694 | A1 | * | 1/2004 | Lutz .............................. 435/239 |
| 2004/0214314 | A1 | * | 10/2004 | Srienc et al. ............. 435/288.7 |

(Continued)

FOREIGN PATENT DOCUMENTS

AU    2008266131 B2    10/2011
EP    2173861 B1    4/2011

(Continued)

OTHER PUBLICATIONS

Dileo, A.J. et al., "Size exclusion removal of model mammalian viruses using a unique membrane system, Part II: Module Qualification and Process Simulation," Biologicals, Academic Press Ltd., London GB, vol. 21, No. 3, pp. 287-296 (1993).

(Continued)

*Primary Examiner* — Walter D Griffin
*Assistant Examiner* — Cameron J Allen
(74) *Attorney, Agent, or Firm* — Alex A. Andalis

(57) ABSTRACT

The invention provides methods for treating cell culture media for use in a bioreactor using ultraviolet C (UVC) light and filtration.

27 Claims, 3 Drawing Sheets

(56) References Cited

U.S. PATENT DOCUMENTS

| | | | |
|---|---|---|---|
| 2004/0248075 A1* | 12/2004 | Yamaguchi et al. | 435/2 |
| 2005/0153420 A1* | 7/2005 | Konz, Jr. et al. | 435/239 |
| 2006/0270017 A1* | 11/2006 | Reiter et al. | 435/235.1 |
| 2009/0130704 A1* | 5/2009 | Gyure | 435/41 |

FOREIGN PATENT DOCUMENTS

| | | |
|---|---|---|
| MX | 286684 | 5/2011 |
| WO | 96/00237 A1 | 1/1996 |
| WO | 02092806 A1 | 11/2002 |
| WO | 03/094978 A1 | 11/2003 |
| WO | 03094978 A1 | 11/2003 |
| WO | 2004/075931 A2 | 9/2004 |
| WO | 2004103530 A1 | 12/2004 |
| WO | 2005/118000 A1 | 12/2005 |

OTHER PUBLICATIONS

Torrentera-Blanco, L. et al., "UV sterilization unit," Investigaciones Marinas Cicimar, vol. 5, no Spec. Issue 1, pp. 19-28 (1990).

Schmidt et al., "An integrated concept for robust and efficient virus clearance and contaminant removal in biotech processes" Bioprocess Intl. (Special suppl), Trends in Integrated Biomanufacturing, vol. 3, No. 9 pp. 26-31 (2005).

Diffey,B, "Sources and measurement of ultraviolet radiation," Methods 28:4-13, 2002.

Gasparro, F. and Brown, D., "Photobiology 102: UV Sources and Dosimetry—the Proper Use and Measurement of 'Photons as a Reagent'," J. Investigative Derm 114:613-615, 2000.

Pharmaceutical CGMPs, "Guidance for Industry," 27-28, 2004.

Wang, R., "Effect of Room Fluorescent Light on the Deterioration of Tissue Culture Medium," In Vitro 12(1):19-22, 1976.

Heering, "UV Sources—Basics, Properties and Applications," *IUVA News* 6(4):7-13, 2004.

Heraeus Noblelight, "Ultraviolette Lampen," product brochure, pp. 1-16, Aug. 28, 2008.

Philips Lighting B.V., "Perfection Preserved by the purest of light," pp. 1-4, product brochure, Sep. 2003.

Mahns et al., "Irradiation of Cells With Ultraviolet-A (320-400 nm) in the Presence of Cell Culture Medium Elicits Biological Effects Due to Extracellular Generation of Hydrogen Peroxide," *Free Radical Research* 37(4): 391-397, 2003.

GE Lighting, "Spectral Power Distribution Curves—Warm White (WW)," General Electric Company website, 2014.

GE Lighting, "Spectral Power Distribution Curves—Daylight (D)," General Electric Company website, 2014.

Stoien and Wang, "Effect of Near-Ultraviolet and Visible Light on Mammalian Cells in Culture II. Formation of Toxic Photoproducts in Tissue Culture Medium by Blacklight," *Proc. Nat. Acad. Sci. USA* 71(10):3961-3965, 1974.

Oberg et al., "Identification of the Tryptophan Photoproduct 6-Formylindolo[3,2-b]carbazole, in Cell Culture Medium, as a Factor That Controls the Background Aryl Hydrocarbon Receptor Activity," *Toxicological Sciences* 85:935-943, 2005.

Romero et al., "Polyphenols in red wine inhibit the proliferation and induce apoptosis of LNCaP cells," *BJU International* 89:950-954, 2002.

Marcarini et al., "Investigation of cytotoxic, apoptosis-inducing, genotoxic and protective effects of the flavonoid rutin in HTC hepatic cells," *Exp Toxicol Pathol* 1-7, 2010.

Lorenzen et al., "Effects of UV Irradiation of Cell Culture Medium on PCB-Mediated Porphyrin Accumulation and EROD Induction in Chick Embryo Hepatocytes," *Toxic in Vitro* 7(2):159-166, 1993.

Berthold et al., "Experimental approaches to guarantee minimal risk of potential virus in purified monoclonal antibodies," *Cytotechnology* 9:189-201, 1992.

Chisti, "Srategies in Downstream Processing," in *Bioseparation and Bioprocessing: A Handbook*, vol. 2, (Subramanian, G., editor), Wiley-VCH, New York, pp. 3-30, 1998.

Dichtelmuller et al., Improvement of Virus Safety of a S/D-Treated Factor VIII Concentrate by Additional Dry Heat Treatment at 100° C, *Biologicals* 24:125-130, 1996.

DiLeo et al., "High Resolution Removal of Virus From Protein Solutions Using a Membrane of Unique Structure," *Bio/Technology* 10:182-188, 1992.

Harbour and Woodhouse, "Viral contamination of monoclonal antibody preparations: Potential problems and possible solutions," *Cytotechnology* 4:3-12, 1990.

Hesse and Wagner, "Developments and improvements in the manufacturing of human therapeutics with mammalian cell cultures," *TIBTECH* 18:173-180, 2000.

Kalyanpur, "Downstream Processing in the Biotechnology Industry," *Molecular Biotechnology* 22:87-98, 2002.

Van Reis and Zydney, "Membrane separations in biotechnology," *Current Opinion in Biotechnology* 12:208-211, 2001.

Walter et al., "Virus Removal and Inactivation," In Validation of Biopharmaceutical Manufacturing Processes; Kelley, B., et al.; ACS Symposium Series; American Chemical Society: Washington, DC, 1998, Ch. 9, pp. 114-124.

Dulbecco, "Dulbecco's Modified Eagle's Medium [DME]," *Sigma-Aldrich* Apr. 2007.

MIDSCI, "Tissue Culture Trouble-Shooting," *Tissue Culture Information and Protocols* pp. 1-4.

CELLnTEC, "PCT Corneal Epithelium Medium, Defined," pp. 1-2, Sep. 29, 2011.

Cabri, "Laboratory Procedures for Microorganisms," *The CABRI Consortium 1999-2013* pp. 1-8, Apr. 2013.

Meridian Life Science, Inc., "Upstream Cell Culture Optimization," 2013.

Notice of Opposition to a European patent—EP 2 173 861, Jan. 20, 2012.

Response to Notices of Opposition to EP Pat. No. 2173861, Oct. 9, 2012.

Summons to Attend Oral Proceedings re EP Pat. No. 2 173861, Sep. 2, 2013.

Opponent Response to Summons to Oral Proceedings dated Sep. 20, 2013, Dec. 4, 2013.

EPEB68372_Letter to EPO, Dec. 4, 2013.

Further Submission of Opponent in Preparation of Oral Proceedings, Jan. 3, 2014.

Results of Oral Hearing Application No. 08770870.7, Feb. 4, 2014.

Tiplon, B. et al., "Retrovirus and parvovirus clearance from an affinity column product using adsorptive depth filtration." BioPharm. Int'l. 15/9 pp. 43-50 (Sep. 2002).

\* cited by examiner

METHODS OF TREATING CELL CULTURE MEDIA FOR USE IN A BIOREACTOR

BACKGROUND OF THE INVENTION

1. Field of the Invention

The invention relates to methods for treating cell culture media for use in a bioreactor using ultraviolet C (UVC) light and filtration.

2. Background of the Invention

Viral contamination of cellular media and supernatants poses a large challenge to biopharmaceutical manufacturers worldwide. Several methods have been employed to inactivate and/or remove large or small, enveloped or non-enveloped (or "naked") DNA or RNA viral particles from cellular supernatants. Examples of these approaches include 20 nm filtration technology, Q membrane chromatography, and depth filter technology. These methods, however, have been used primarily as a means for viral inactivation (i.e., viral clearance) of media and supernatants collected from cell lines or tissues (i.e., downstream of protein production).

Such viral clearance methods have not been used to treat cell culture media prior to exposure to cell lines or tissues (i.e., upstream of protein production) for several reasons. First, employing such techniques to the treatment of large-scale cellular media, where up to 20,000 L of cellular media is processed per day, can be prohibitive in terms of time and cost. Second, such methods have historically been employed to remove contaminants from large-scale cellular supernatants as a preliminary step in the purification of therapeutic protein products from the large-scale cellular supernatants prior to administration of the therapeutic protein products to patients. Third, there has been no required or documented need in the art for the inactivation or removal of viral particles in the upstream process of protein production. Finally, bioreactors and fermenters are frequently not equipped with the machinery required to carry out these techniques, and the cost of retrofitting exisiting equipment to add such machinery can be exorbitantly high.

In addition to the above techniques, ultraviolet light has been used to treat large-scale protein preparations prior to the purification of these proteins from cellular supernatants. However, as with other methods of treating large-scale cellular supernatants prior to the purification and isolation of therapeutic protein products from the cellular supernatants, ultraviolet light exposure has been used primarily downstream of protein production. In other words, no prior art methods exist in which ultraviolet light (alone or in combination with other purification or treatment methods) has been used to treat cell culture media prior to introducing the cell culture media into a bioreactor. Thus, there is a need in the art for methods for treating cell culture media for use in a bioreactor. Such methods would be particularly useful for protecting valuable cell lines from viral contamination, saving costs lost as a result of contaminated and unusable media, and increasing the efficiency of protein production by such cell lines. Therefore, the development of such methods would have wide application in the manufacture of biopharmaceuticals.

SUMMARY OF THE INVENTION

The present invention provides methods for treating cell culture media for use in a bioreactor comprising exposing the cell culture media to ultraviolet C (UVC) light; passing the cell culture media through a sterile filter; and introducing the cell culture media into a bioreactor.

The present invention also provides methods of treating cell culture media for use in a bioreactor comprising exposing the cell culture media to UVC light; passing the cell culture media through a depth filter; passing the cell culture media through a sterile filter; and introducing the cell culture media into a bioreactor.

Specific preferred embodiments of the present invention will become evident from the following more detailed description of certain preferred embodiments and the claims.

DETAILED DESCRIPTION OF THE INVENTION

The invention provides methods for treating cell culture media for use in a bioreactor comprising exposing the cell culture media to ultraviolet C (UVC) light; passing the cell culture media through a sterile filter; and introducing the cell culture media into a bioreactor. The invention also provides methods of treating cell culture media for use in a bioreactor comprising exposing the cell culture media to UVC light; passing the cell culture media through a depth filter; passing the cell culture media through a sterile filter; and introducing the cell culture media into a bioreactor.

Figure 1:
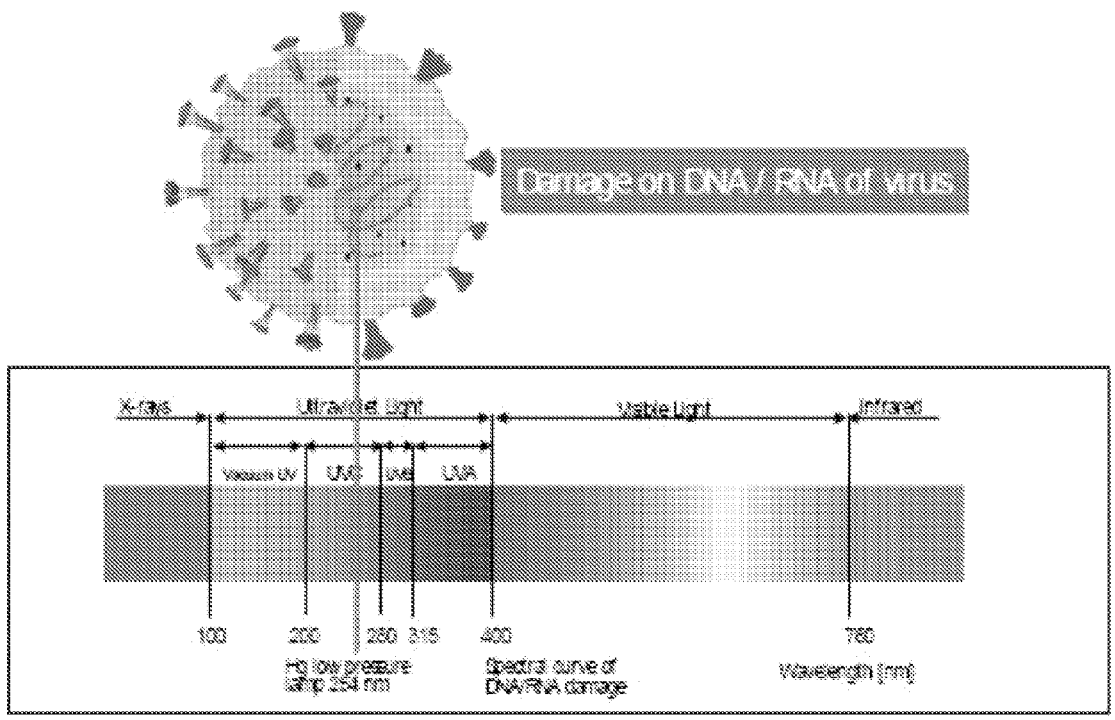
FIG. 1 shows the relationship between the wavelength of light and viral DNA/RNA damage.

In the methods of the invention, cell culture media is exposed to UVC light prior to introducing the cell culture media into a bioreactor. The term "ultraviolet light" refers to a section of the electromagnetic spectrum of light extending from the x-ray region (100 nm) to the visible region (400 nm). In particular, ultraviolet light is generally divided into four fractions: (1) vacuum ultraviolet light—having a wavelength of 100 to 200 nm, (2) ultraviolet C (UVC)—having a wavelength of 200 to 280 nm, (3) ultraviolet B (UVB)—having a wavelength of 280 to 315 nm, and (4) ultraviolet A (UVA)—having a wavelength of 315 to 400 nm (see FIG. 1).

In one embodiment of the invention, cell culture media is exposed to UVC light having a wavelength of between 200 and 280 nm prior to introducing the cell culture media into a bioreactor. In another embodiment of the invention, cell culture media is exposed to UVC light having a wavelength of 254 nm prior to introducing the cell culture media into a bioreactor. In other embodiments of the invention, cell culture media is exposed to UVC light having a wavelength of 254 nm+/−1 nm, or a wavelength of 254 nm+/−2 nm, or a wavelength of 254 nm+/−3 nm, or a wavelength of 254 nm+/—4 nm, or a wavelength of 254 nm+/−5 nm, or a wavelength of 254 nm+/−6 nm, or a wavelength of 254 nm+/−7 nm, or a wavelength of 254 nm+/−8 nm, or a wavelength of 254 nm+/−9 nm, or a wavelength of 254 nm+/−10 nm, or a wavelength of 254 nm+/−15 nm, or a wavelength of 254 nm+/−20 nm, or a wavelength of 254 nm+/−25 nm.

In the methods of the invention, UVC light is used to inactivate non-enveloped viral particles by damaging viral DNA or RNA. Nucleic acid damage inactivates viruses and prevents subsequent replication. A typical device—or UVC reactor—for exposing solutions to UVC light utilizes hydraulic spiral flow along an irradiation source that generates Dean vortices in a fluid stream that allows doses of UVC irradiation to be delivered uniformly throughout the solution. When UVC light is used to inactivate non-enveloped viral particles, viral inactivation generally occurs after about five minutes of exposure.

As described herein, viral clearance methods known in the art have been used almost exclusively downstream of protein production. In addition to cost and time considerations, such methods have been used almost exclusively downstream of protein production because the objective of such methods has been to inactivate and/or remove viral particles in large-scale cellular supernatants prior to the purification and isolation of therapeutic protein products from the cellular supernatants. With respect to the use of UVC light to inactivate viral particles in large-scale bioprocesses, one reason for the lack of prior art processes employing UVC light exposure upstream of protein production has been the high absorption of UVC light by cell culture media at 254 nm, and the effects of this high absorption on the ability of such media to support efficient cell growth. The methods of the invention avoid this problem by increasing the energy of the UVC light being used.

The term "energy" refers to the amount of ultraviolet radiation in Joules/meters$^2$ to which treated cell culture media is exposed. In one embodiment of the invention, cell culture media is exposed to UVC light at an energy density of 120-320 J/m$^2$ prior to introducing the cell culture media into a bioreactor. In another embodiment, cell culture media is exposed to UVC light at an energy density of 238 J/m$^2$ prior to introducing the cell culture media into a bioreactor. In other embodiments of the invention, the cell culture media is exposed to UVC light at an energy density of 238 J/m$^2$+/−1 J/m$^2$, or at an energy density of 238 J/m$^2$+/−2 J/m$^2$, or at an energy density of 238 J/m$^2$+/−3 J/m$^2$, or at an energy density of 238 J/m$^2$+/−4 J/m$^2$, or at an energy density of 238 J/m$^2$+/−5 J/m$^2$, or at an energy density of 238 J/m$^2$+/−10 J/m$^2$, or at an energy density of 238 J/m$^2$+/−15 J/m$^2$, or at an energy density of 238 J/m$^2$+/−20 J/m$^2$, or at an energy density of 238 J/m$^2$+/−25 J/m$^2$, or at an energy density of 238 J/m$^2$+/−30 J/m$^2$, or at an energy density of 238 J/m$^2$+/−40 J/m$^2$, or at an energy density of 238 J/m$^2$+/−50 J/m$^2$, or at an energy density of 238 J/m$^2$+/−60 J/m$^2$, or at an energy density of 238 J/m$^2$+/−70 J/m$^2$.

The methods of the invention can be used for bench-scale inactivation processes, but more significantly for large-scale treatment of cell culture media prior to introducing the cell culture media into a bioreactor. In one embodiment of the invention, cell culture media is exposed to UVC light at a flow rate of 1-12 liters per hour prior to introducing the cell culture media into a bioreactor. In another embodiment of the invention, cell culture media is exposed to UVC light at a flow rate of 6 liters per hour prior to introducing the cell culture media into a bioreactor. In other embodiments of the invention, cell culture media is exposed to UVC light at a flow rate of 6 liters per hour+/−1 liter per hour, or at a flow rate of 6 liters per hour+/−2 liters per hour, or at a flow rate of 6 liters per hour+/−3 liters per hour, or at a flow rate of 6 liters per hour+/−4 liters per hour, or at a flow rate of 6 liters per hour+/−5 liters per hour.

"Log reduction value" (LRV) is a measurement of filtration retention efficiency that is equivalent to the ratio of the log of the challenge concentration divided by the filtrate concentration (LRV=Log$_{10}$ Challenge/Filtrate). In the present invention, the challenge concentration refers to the concentration of viral materials in the cell culture media. For purposes of the invention, a filtrate (i.e., cell culture media) is considered to be sterile if it has an LVR of at least 4.85, and filtrates having LRV's of between 6 and 7 are preferred. In one embodiment of the invention, a log reduction value of greater than or equal to 4.85 is obtained following the treatment of cell culture media. In another embodiment, a log reduction value of between 6 and 7 is obtained following the treatment of cell culture media.

In the methods of the invention, cell culture media is subjected to filtration step after being exposed to UVC light. The term "sterile filtration" or "sterile filter" refers to the removal of micro plasma and other potential contaminants from cell culture media through use of a standard biological sterile filter. In one embodiment of the invention, cell culture media is passed through a sterile filter having pores with a maximum size of 200 nm prior to introducing the cell culture media into a bioreactor.

In another embodiment of the invention, cell culture media is passed through a depth filter. The term "depth filter" refers to a filter that has multiple filtration layers, each layer being responsible for the filtration of particulate matter of different sizes and densities. This type of filtration process is similar to size exclusion. Light material is isolated at the top of the filter bed. The media becomes progressively finer and denser in the lower layers. Larger suspended particles are removed in the upper layers, while smaller particles are removed by lower layers.

The ability of depth filters to remove certain types of viral particles is dependent on the pH of the solution being filtered. For example, when cell culture media having a lower pH is passed through a depth filter, non-enveloped viral particles can be more efficiently cleared from the media. Cell culture media normally has a high conductivity of about 15 to 20 mS/cm and pH 7.4, which aids in the capture of enveloped viral particles. Performing filtration at conditions of neutral pH would therefore ensure higher LRV's for enveloped viruses, which have pIs of 6.0-7.8, In one embodiment of the invention, the cell culture media is passed through the depth filter at an acidic pH. In another embodiment of the invention, the cell culture media is passed through the depth filter at pH 5.0, In other embodiments of the invention, the cell culture media is passed through the depth filter at a pH of between 4.0-5.0, or at a pH of between 5.0-6.0, or at a pH of between 6.0-7.0.

The methods of the invention can be used to inactivate viral particles that may be present in cell culture media prior to introducing the cell culture media into a bioreactor. Other methods of the invention can be used to also remove viral particles (including viral particles that may not have been inactivated by exposure to UVC light). In one method of the invention, cell culture media is exposed to UVC having a wavelength or energy, or at a flow rate, sufficient to damage the nucleic acids of any non-enveloped viruses in the cell culture media. In another method of the invention, cell culture media is passed through a depth filter having a pore size, or at a flow rate, sufficient to remove any enveloped viruses from the cell culture media.

In the methods of the invention, cell culture media is treated prior to introducing the cell culture media into a bioreactor. The term "bioreactor" refers to a device or system for use in the large-scale growth of cell lines or tissues for the preparation of biopharmaceuticals. For example, a typical bioreactor can be used to generate 200 to 20,000 L of cellular supernatant (containing the intended byproduct of the bioprocess, a biopharmaceutical protein). In the methods of the invention, the bioreactor can be used to support the growth of cells for the large-scale production of, for example, antibodies.

The present invention provides a method for inactivating and/or removing viral particles from cell culture media upstream of the introduction of the cell culture media into a bioreactor. One of the benefits of the present invention is that by treating cell culture media upstream of its introduction into the bioreactor, the risk of contamination at the point of inoculation can be reduced, thereby creating a better environment for maximum cell growth and maximum protein production (e.g., antibody titer). In addition, the present invention can be used to lower the risk of lost production costs (e.g., associated with a maintenance shutdown of a biopharmaceutical manufacturing process following viral contamination).

The treated cell culture media can be used to support the growth of a number of different cell types. In one embodiment of the invention, the treated cell culture media is used to support the growth of mammalian cells. In another embodiment of the invention, the mammalian cells are capable of producing antibodies. In yet another embodiment of the invention, the treated cell culture media is used to support the growth of insect cells.

The Examples that follow are illustrative of specific embodiments of the invention, and various uses thereof. They are set forth for explanatory purposes only, and are not to be taken as limiting the invention.

EXAMPLE 1

Characteristics of Cell Culture Media

The methods of the invention can be used to treat cell culture media for use in a bioreactor. Three types of cell culture media were analyzed for osmolality, conductivity at 25° C., and absorbance at 254 nm (see Table I).

TABLE I

| Media Type | Osmolality (mOsm/kg) | Conductivity (mS/cm) 25° C. | Absorbance O.D. 254 nm |
| --- | --- | --- | --- |
| A | 296.33 | 12.19 | 4.8 |
| B | 296.67 | 11.05 | 11.7 |
| C | 854.67 | 12.11 | 64 |

EXAMPLE 2

Viral Inactivation by UVC Light

Studies have been conducted to determine the inactivation of several viruses by UVC light. Table II shows the model viruses that were chosen: Xenotropic murine leukemia virus (x-MuLV), Murine minute virus (MMV), Porcine parovirus (PRV), and Reovirus 3 (Reo 3).

TABLE II

| Model | Family | Properties | pI |
| --- | --- | --- | --- |
| x-MuLV | Retroviridae | Enveloped, ss RNA, 80-120 nm low resistance | 6.0-6.7 |
| MMV | Paroviridae | Non-enveloped, ss DNA, 18-26 nm, high resistance | 5.0 |
| PRV | Herpesviridae | Enveloped, ds DNA, 120-200 nm, low-medium Resistance | 7.4-7.8 |
| Reo 3 | Reoviridae | Non-enveloped, ds RNA, 50-70 nm, medium resistance | 3.9 |

Inactivation of MMV(i) and MMV(p) in production media was conducted at various flow rates. Inactivation was achieved with an LRV of greater than 4.85 for MMV(p) (see Table III) and an LRV of greater than 3.35 for MMV(i) (see Table IV).

TABLE III

| MMVp inactivation profile using UVC light | | | | | | | |
| --- | --- | --- | --- | --- | --- | --- | --- |
| A254 nm | Flow rate lab scale unit (L/hr) | UVC lamp covered (%) | Expected fluency (J/m$^2$) | MVMp inactivation [LRV] | Flow rate (ml/min) | Time for media collection (min/250 ml) | Process Scale (L/hr) |
| 12 | 10 | 0 | 143.1 | 3.93, 4.09, 4.09 | 166.7 | 1.5 | 1000-2000 |
| 12 | 8 | 0 | 178.9 | 4.76, 4.76, 4.76 | 133.3 | 1.9 | 1000-2000 |
| 12 | 6 | 0 | 238.5 | ≥4.85, ≥4.85, ≥4.85 | 100 | 2.5 | 1000-2000 |

TABLE IV

| MMVi inactivation profile using UVC light | | | | | | | |
| --- | --- | --- | --- | --- | --- | --- | --- |
| A254 nm | Flow rate lab scale unit (L/hr) | UVC lamp covered (%) | Expected fluency (J/m$^2$) | MVMi inactivation [LRV] | Flow rate (ml/min) | Time for media collection (min/250 ml) | Process Scale (L/hr) |
| 12 | 10 | 0 | 143.1 | ≥3.35, ≥3.35, ≥3.35 | 166.7 | 1.5 | 1000-2000 |
| 12 | 8 | 0 | 178.9 | ≥3.35, ≥3.35, ≥3.35 | 133.3 | 1.9 | 1000-2000 |
| 12 | 6 | 0 | 238.5 | ≥3.35, ≥3.35, ≥3.35 | 100 | 2.5 | 1000-2000 |

These assays were repeated for inactivation of MuLV from both production media and feed media. The results of these assays (i.e., LRVs of less than 1) suggest that an additional inactivation or removal step may further enhance the methods of the invention (see Tables V and VI).

TABLE V

MuLV inactivation profile using UVC light (production media)

| A254 nm | Flow rate lab scale unit (L/hr) | UVC lamp covered (%) | Expected fluency (J/m$^2$) | MVMp inactivation [LRV] | Flow rate (ml/min) | Time for media collection (min/250 ml) | Process Scale (L/hr) |
|---|---|---|---|---|---|---|---|
| 12 | 10 | 0 | 143.1 | 0, 0, 0 | 166.7 | 1.5 | 1000-2000 |
| 12 | 8 | 0 | 178.9 | 0, 0, 0 | 133.3 | 1.9 | 1000-2000 |
| 12 | 6 | 0 | 238.5 | 0, 0, 0 | 100 | 2.5 | 1000-2000 |

TABLE VI

MuLV inactivation profile using UVC light (feed media)

| A254 nm | Flow rate lab scale unit (L/hr) | UVC lamp covered (%) | Expected fluency (J/m$^2$) | MVMp inactivation [LRV] | Flow rate (ml/min) | Time for media collection (min/250 ml) | Process Scale (L/hr) |
|---|---|---|---|---|---|---|---|
| 64 | 2 | 0 | 62 | 0, 0, 0 | 33.3 | 7.5 | 1000-2000 |
| 64 | 2 | 0 | 62 | 0, 0, 0 | 33.3 | 7.5 | 1000-2000 |
| 64 | 2 | 0 | 62 | 0, 0, 0 | 33.3 | 7.5 | 1000-2000 |

EXAMPLE 3

Viral Removal Using Depth Filtration

Studies have been conducted on removal of enveloped viral particles as well as other unwanted cellular materials from cell-culture media by using a depth filter. Table VII shows viral inactivation of three enveloped viruses as well as a non-enveloped virus. The LRVs determined from these studies show that the depth filter can efficiently remove enveloped viral particles from cell culture media.

TABLE VII

| Removal method | PRV | x-MuLV | MMV | Reo 3 |
|---|---|---|---|---|
| Depth filter | 3.17 | >4.23 | 4.13 | >5.01 |
| 20 nm filter | >5.04 | >4.87 | 4.47 | 5.35 |
| Q membrane | 3.89 | >4.24 | 4.47 | 5.35 |

Figure 2:
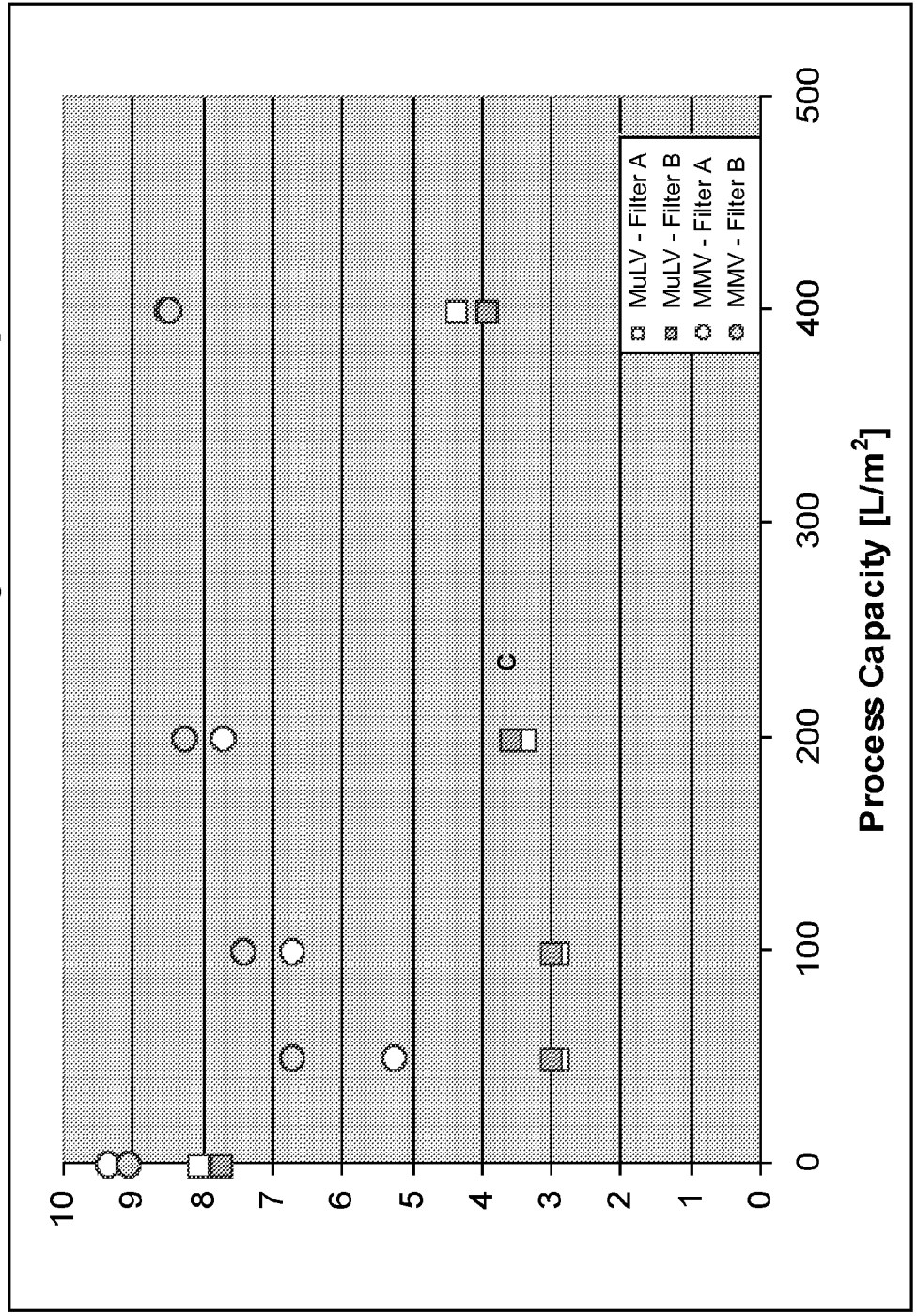
FIG. 2 shows the efficiency of removal of murine leukemia virus (MuLV) or minute mouse virus (MMV) from cell culture media using two types of depth filters.
Figure 3:
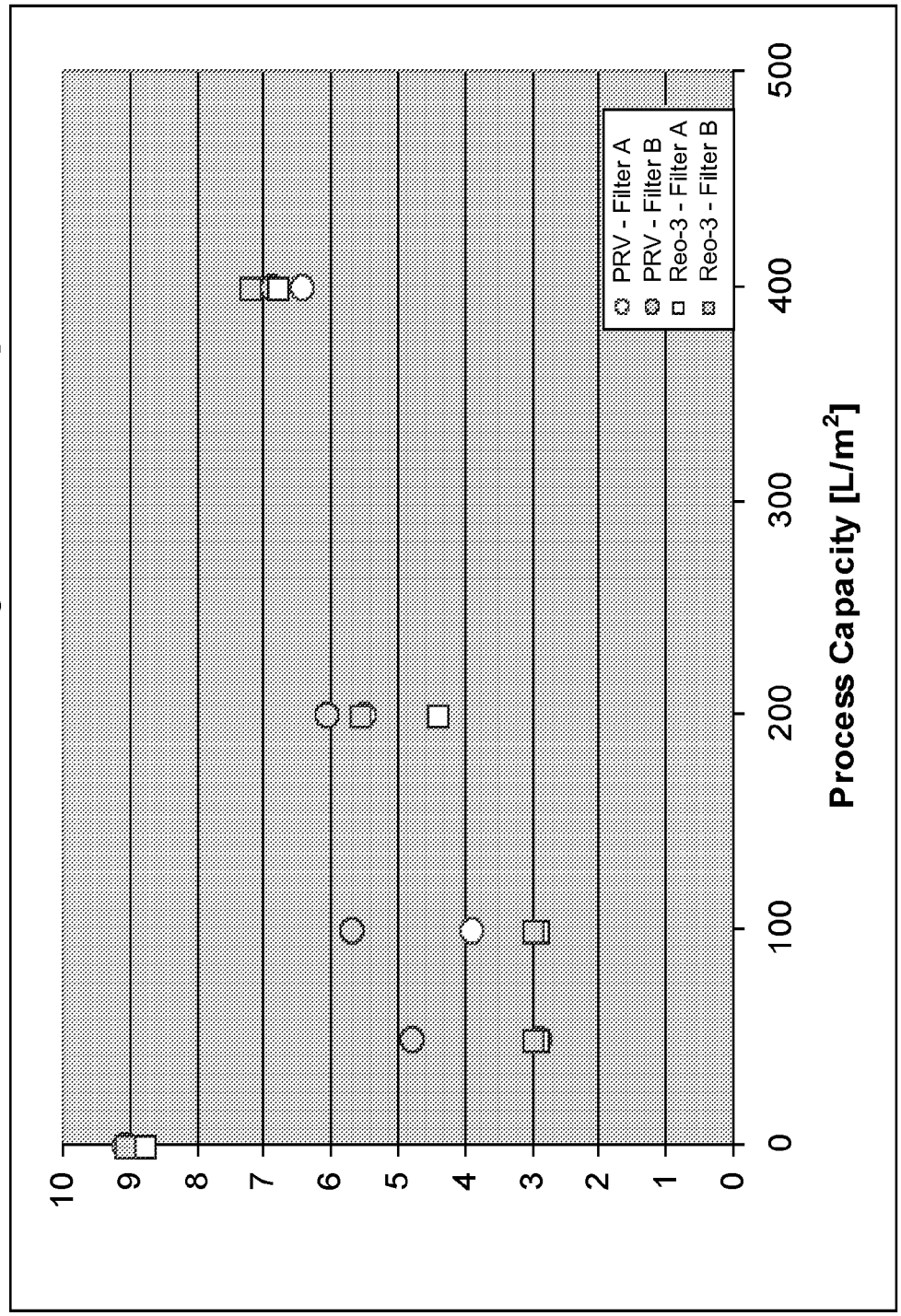
FIG. 3 shows the efficiency of removal of porcine parvovirus (PRV) and reovirus 3 (Reo-3) from cell culture media using two types of depth filters.

Two types of depth filters were tested for efficiency in removing viral particles (see FIGS. 2 and 3).

The section headings used herein are for organizational purposes only and are not to be construed as limiting the subject matter described. All references cited in this application are expressly incorporated by reference herein.

What is claimed is:

1. A method of treating cell culture media for use in a bioreactor comprising: (a) exposing the cell culture media to ultraviolet C (UVC) light at an energy density of 120-320 J/m$^2$; (b) passing the UVC-treated cell culture media through a sterile filter; and (c) introducing the filtered, UVC-treated cell culture media into a bioreactor.

2. The method of claim 1, wherein the UVC light has a wavelength of 254 nm.

3. The method of claim 1, wherein the cell culture media is exposed to UVC light at a flow rate of 1-12 liters per hour.

4. The method of claim 3, wherein the flow rate is 6 liters per hour.

5. The method of claim 1, wherein the log reduction value is greater than or equal to 4.85.

6. The method of claim 5, wherein the log reduction value is 6-7.

7. The method of claim 1, wherein the cell culture media is exposed to UVC light at an energy density of 238 J/m$^2$.

8. The method of claim 1, wherein the sterile filter has pores with a maximum size of 200 nm.

9. The method of claim 1, wherein the step of exposing the cell culture media to UVC light is sufficient to damage the nucleic acids of any non-enveloped viruses in the cell culture media.

10. The method of claim 1, wherein the treated cell culture media is used to support the growth of mammalian cells.

11. The method of claim 10, wherein the mammalian cells are capable of producing antibodies.

12. The method of claim 1, wherein the treated cell culture media is used to support the growth of insect cells.

13. A method of treating cell culture media for use in a bioreactor comprising: (a) exposing the cell culture media to ultraviolet C (UVC) light at an energy density of 120-320 J/m$^2$; (b) passing the UVC-treated cell culture media through a depth filter; (c) passing the cell culture media through a sterile filter; and (d) introducing the filtered, UVC-treated cell culture media into a bioreactor.

14. The method of claim 13, wherein the UVC light has a wavelength of 254 nm.

15. The method of claim 13, wherein the cell culture media is exposed to UVC light at a flow rate of 1-12 liters per hour.

16. The method of claim 15, wherein the flow rate is 6 liters per hour.

17. The method of claim 13, wherein the log reduction value is greater than or equal to 4.85.

18. The method of claim 17, wherein the log reduction value is 6-7.

19. The method of claim 13, wherein the cell culture media is exposed to UVC light at an energy density of 238 J/m$^2$.

20. The method of claim 13, wherein the cell culture media is passed through the depth filter at an acidic pH.

21. The method of claim 20, wherein the cell culture media is passed through the depth filter at pH 5.0.

22. The method of claim 13, wherein the sterile filter has pores with a maximum size of 200 nm.

23. The method of claim 13, wherein the step of exposing the cell culture media to UVC light is sufficient to damage the nucleic acids of any non-enveloped viruses in the cell culture media.

24. The method of claim 13, wherein the step of passing the cell culture media through a depth filter is sufficient to remove any enveloped viruses from the cell culture media.

25. The method of claim 13, wherein the treated cell culture media is used to support the growth of mammalian cells.

26. The method of claim 13, wherein the mammalian cells are capable of producing antibodies.

27. The method of claim 13, wherein the treated cell culture media is used to support the growth of insect cells.

\* \* \* \* \*